United States Patent [19]

Koss

[11] 4,411,260
[45] Oct. 25, 1983

[54] PENIS PROSTHESIS

[76] Inventor: Walter Koss, Industriestrasse, D-6222 Geisenheim, Fed. Rep. of Germany

[21] Appl. No.: 324,008

[22] Filed: Nov. 23, 1981

[30] Foreign Application Priority Data

Nov. 24, 1980 [DE] Fed. Rep. of Germany ... 8031230[U]

[51] Int. Cl.³ .............................................. A61F 5/00
[52] U.S. Cl. .............................................. 128/79; 3/1
[58] Field of Search .................................. 128/79; 3/1

[56] References Cited

U.S. PATENT DOCUMENTS

| 3,832,996 | 9/1974 | Kalnberz | 128/79 |
| 4,066,073 | 1/1978 | Finney et al. | 128/79 |
| 4,187,839 | 2/1980 | Nuwayser et al. | 128/79 |

*Primary Examiner*—Dalton L. Truluck
*Attorney, Agent, or Firm*—Gifford, VanOphem, Sheridan & Sprinkle

[57] ABSTRACT

A penis prosthesis is in the form of a flexible rod member comprising implantable plastic material, at least in the outer region thereof. The rod member is subdivided into at least two portions, and one portion is provided at the junction location or locations with a tubular extension portion which can be pushed over the other of the portions.

12 Claims, 6 Drawing Figures

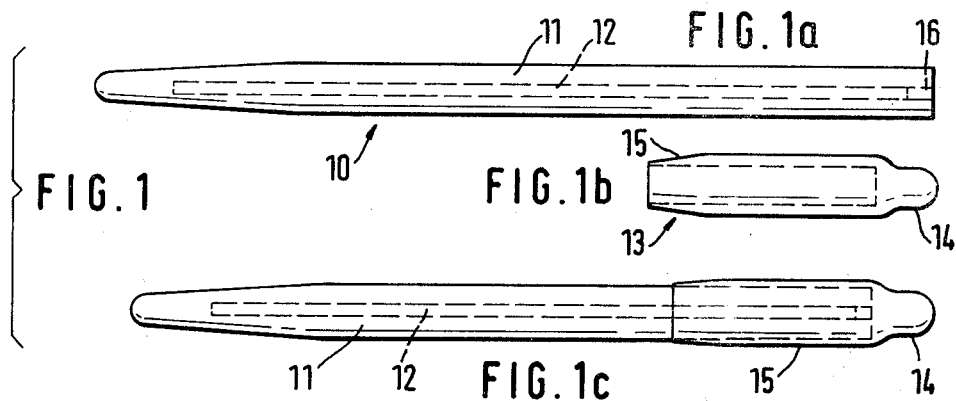
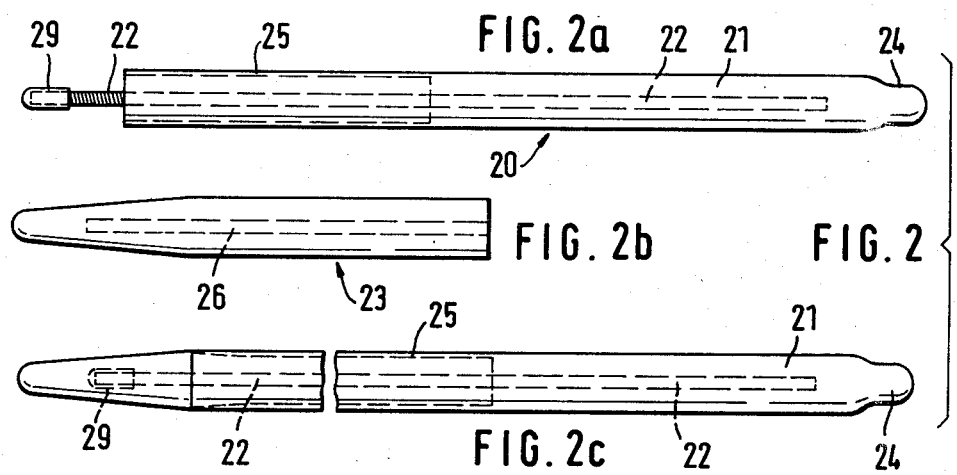
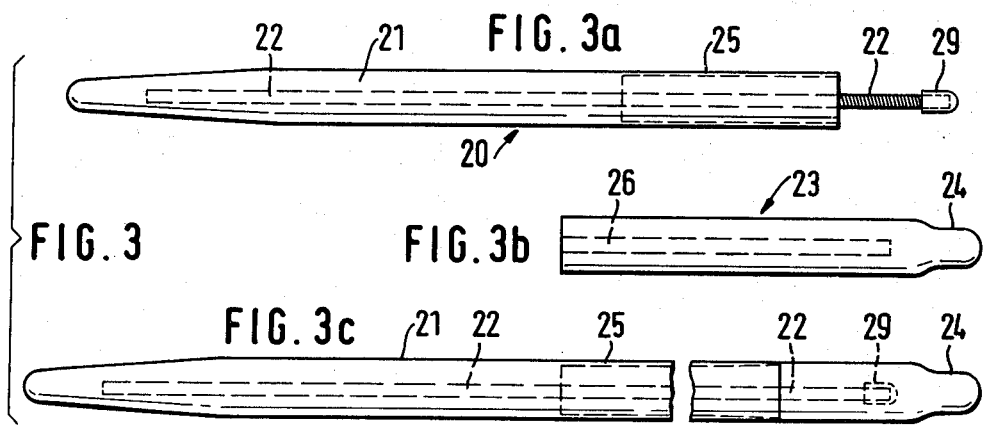

PENIS PROSTHESIS

BACKGROUND OF THE INVENTION

The invention relates to a penis prosthesis in the form of a flexible rod member which comprises implantable plastic material, at least in the outer region thereof.

Such prostheses are known (DE-GS No. 78 05 284). They are implanted in pairs into the respective erectile or corpora cavernosa, for treating impotence in the case of neurological illnesses, vascular illnesses, injuries and in other situations. Preferably, such prostheses have a core portion which comprises for example synthetic material or also twisted-together high-purity silver wires which do not suffer from hardening when subjected to bending. After the flexible rod members are implanted, the penis can be bent into the respective shape and position desired.

The known prostheses of the above-indicated or a similar kind have been highly successful in practice in many situations. There is the difficulty however that, for the purposes of implanting the prosthesis, the operator must use rod members which are precisely adapted both in respect of thickness and also more particularly in respect of length, to the anatomical circumstances of the patient. It is therefore necessary to make provision for an assortment of pairs of rod members of for example seven or more different lengths, in each of two or even more diameter ranges of for example 9.5 mm. However, providing such an assortment of members is so costly that frequently the appropriate initial capital investment is not made, for financial reasons. However, compromises in regard to properly adapting the prosthesis to a patient can have disadvantageous consequences for the patient.

Simply shortening the prosthesis rod members shortly before the implantation operation encounters difficulties because it is not possible to ensure a clean, smooth, rounded external shape, under the conditions obtaining in the operating theatre and in consideration of the need for haste. This applies in particular when the prosthesis rod members have an inner core because in that case either the core also has to be reduced in length and accordingly is no longer enclosed by the plastic material, or the rod member is required to have a portion without a core, to permit the rod member properly to be reduced in length. In that case however, that portion of the rod member does not have the inner support formed by the core.

The attempt has also already been made to provide prosthesis rod members of different lengths, by fitting on portions of different lengths. However, the gap which is formed when the portions are fitted together gives rise to the danger of tissue being caught in the gap, when the penis prosthesis is bent. This can give rise to necroses and other disadvantageous consequences.

SUMMARY OF THE INVENTION

An object of the present invention is therefore to provide an implantable penis prosthesis in the form of a flexible rod member which permits the operator to adapt it in respect of length and/or diameter.

To achieve this and other objects, the invention is based on a prosthesis of the kind set forth at the beginning of this specification, and is characterised in that the rod or bar member is subdivided in respect of length into at least two portions, and that, at the junction or junctions, the one portion has a tubular extension portion which receives and overlaps an end of the other portion, whereby the extension portion can be pushed over the other portion. After the portion without the tubular extension portion has been shortened to adapt the prosthesis to the anatomical circumstances of the patient, the tubular extension portion can then be pushed on by the operator before the implantation operation, whereby on the one hand the core which has possibly been cut to length or cut off is covered at its end and on the other hand there is no gap formed, which involves the danger of pieces of tissue being nipped in the gap when the prosthesis is bent. It has been found that, if the diameter of the rod member and the tubular extension portion are of the correct dimensions, an absolutely sealed and mechanically very strong connection is formed between the components, some time after the tubular extension portion is pushed into place. There is scarcely any possibility of the components coming apart or twisting relative to each other. Accordingly, the assembled rod members behave in the same manner as the one-piece rod members, both in the implantation operation and also after implantation. The wall thickness of the tubular extension portion and possibly the diameter of the rod member to be joined thereto can be modified to produce rod members of the desired thicknesses. For example, when the inside diameter of the tubular extension portion is 5 mm, wall thicknesses of the tubular extension portion of from 0.5 to 5 mm result in an overall diameter of between 6 and 15 mm.

Further aspects and embodiments of the invention are set forth in the subsidiary claims. Thus, the portion which is provided with the tubular extension portion can be formed as a short soft tip and can form the distal end of the prosthesis.

If the prosthesis is provided in known manner with a core which is of such a construction in at least one portion thereof that it remains in any shape produced by bending, and a sleeve of implantable material, then it is possible for the portion which is provided with the tubular extension portion to have therein a core which projects into or beyond the tubular extension portion, and for the associated other portion to have a central bore for receiving the core. This arrangement thus provides a continuous core in both portions of the prosthesis which accordingly performs in the same manner as a one-piece rod member. A cap can be fitted onto the free end of the core, to hold the end together, particularly when the core comprises twisted wires. The portion having the central bore can be of such a configuration that it forms the distal end or the proximal end. In addition, in a development of the invention, the member may have a middle portion which is provided at both ends with a tubular extension portion, and both a proximal and a distal portion may be fitted thereto, each of said proximal and distal portions having a respective bore for receiving the core in the middle portion. In that case, the prosthesis rod member comprises three portions, so that adaptation in respect of the length of the rod member can be effected at a number of locations thereon.

A further embodiment provides that the rod member has a soft or pliant distal portion, a stiffer middle portion and a very stiff proximal portion. This arrangement can be achieved for example by suitable dimensioning of the core, while the core may also be entirely omitted in the soft distal portion. Subdivision of the rod member in this manner results in the rod member being better adapted to the natural circumstances, with the stiffer middle portion preventing bending or kinking and the very stiff proximal portion providing for good support at the pelvis.

It is in itself desirable for the plastic material forming the sleeve to be comparatively soft or pliant so that the implanted rod members are not conspicuous or cannot be felt. However, a soft sleeve gives rise to the danger that the penis may bend or wires may escape from their enclosure, in sexual intercourse. Therefore, a development of the invention provides that the sleeve has an inner layer which comprises a harder material and which surrounds the core, and an outer layer which comprises a softer material. Instead of the softer outer layer, it is also possible for an outer layer to be disposed at a radial spacing from the harder layer on the core, in which case a plastic gel or a fluid can possibly be introduced into the space between the inner and the outer layers.

The invention will now be described with reference to the accompanying drawings.

BRIEF DESCRIPTION OF THE DRAWINGS

FIG. 1 shows an embodiment of the invention,
FIG. 2 shows a further embodiment of the invention,
FIG. 3 shows a third embodiment of the invention.

DESCRIPTION OF THE PREFERRED EMBODIMENT

Figure 4:
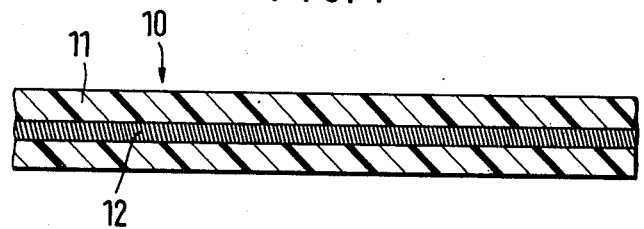
FIGS. 4, 5 and 6 show cross-sectional views of three different embodiments.

Referring to FIGS. 1a and 1b, shown therein are two portions of a prosthesis rod member which can be fitted together. FIG. 1c shows the two portions in the condition of being fitted together. The longer portion 10 shown in FIG. 1a has a sleeve 11 of implantable plastic material, for example silicone or another elastomer, and an embedded core 12 which comprises silver wires which are twisted or stranded together. The shorter portion 13 which subsequently forms the distal end of the prosthesis rod member has a soft tip 14 with an adjoining tubular extension portion 15 which is formed integrally from implantable plastic material. The longer portion 10 can be shortened to the desired length, at the end thereof which is to the right in the drawing. The tubular extension portion 15 is then pushed onto the portion 10, possibly after having been enlarged with a spreading tongs tool and wetting with distilled water. After some time, the two portions form a virtually inseparable flexible rod member as shown in FIG. 1c.

In order to ensure that the core 12 does not project from the portion 10 after the portion 10 has been reduced in length, the sleeve 11 can be axially compressed or upset before the core is cut, so that, after the core has been cut off, the end thereof is retracted into a short passage 16.

In regard to the embodiment shown in FIG. 2, FIG. 2a again shows the longer portion 20 of the prosthesis rod member, FIG. 2b shows the shorter portion 23 and FIG. 2c shows the finished prosthesis rod or bar member. The longer portion 20 which subsequently forms the distal end of the prosthesis has a sleeve 21 of plastic material with a soft tip 24 at the distal end and a core 22, similarly to the core 12 in FIG. 1. At the proximal end (at the left in FIG. 2), the portion 20 has a tubular extension portion 25. The core 22 projects from the tubular extension portion 25. In order to ensure that the wires of the core do not become loose, a cap 29 comprising for example Teflon is fitted onto the end thereof. The shorter portion 23 shown in FIG. 2b has a central bore 26 which receives the free end of the core 22 in the portion 20, including the cap 29, as can be seen from FIG. 2c. The portion 20 can be produced with different diameters and thus wall thicknesses in respect of the tubular extension portion 25 so as to permit adaptation in respect of thickness, besides adaptation in respect of length.

When shortening the two portions 20 and 23 including the core 22, the mode of procedure is such that the core 22 with the cap 29 fills the bore 26 virtually as far as the end thereof, so as to provide satisfactory support.

The embodiment shown in FIG. 3 substantially corresponds to that shown in FIG. 2. The two portions have simply been interchanged, that is to say, the proximal portion 20 now carries the tubular extension portion 25 and the distal portion 23 has the bore 26 and the soft tip 24.

FIG. 4 is a diagrammatic view of a portion of a prosthesis rod member, for example a part of the rod member 10 shown in FIG. 1. Arranged in the sleeve 11 of plastic material is the core 12 which comprises for example stranded silver wires.

Figure 5:
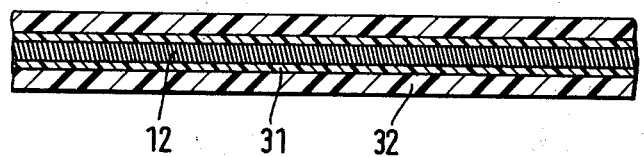

FIG. 5 shows an advantageous modified form of the prosthesis rod member, wherein a layer 31 of comparatively hard plastic material, for example silicone, is first put onto the core 12. The layer 31 acts as a stiffening and protective layer which prevents the core or individual wires from sticking out. Arranged on the inner layer 31 is an outer layer 32 of comparatively soft plastic material, for example silicone, which ensures that the rod member is more readily adapted and cannot be felt.

Figure 6:
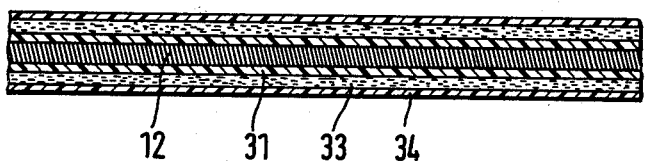

The further alternative form shown in FIG. 6 also has a core 12 with an inner protective layer 31. In a radially outward direction, the inner layer 31 is then followed by an annular space or chamber 33 which is filled with a gel or a fluid, and that space 33 is in turn followed by an outer plastic layer 34 which in turn can be comparatively hard. The gel can be made softer or harder, as desired. The annular space 33 can optionally also be filled simply with air.

What is claimed is:

1. A penis prosthesis in the form of a flexible rod member which comprises implantable plastic material at least in the outer region, characterized in that the rod member is subdivided into at least two portions and having means for connecting said at least two portions comprising one portion having a tubular extension portion at one end adapted to receive and overlap an end of at least one other of said at least two portions, whereby said extension portion is adapted to be pushed over said at least one other portion.

2. A penis prosthesis as set forth in claim 1 characterized in that the portion which is provided with the tubular extension portion comprises a short, soft tip at its other end and forms the distal end of the prosthesis.

3. A penis prosthesis as set forth in claim 1 wherein at least one of said at least two portions is characterized by a core made of a flexible, shape retaining material and a sleeve made of implantable material surrounding said core.

4. A penis prosthesis as set forth in claim 3 characterized in that said at least one of said at least two portions comprises the portion provided with the tubular extension portion, the core extending into the tubular extension portion, and the said at least one other portion having a central bore for receiving the core.

5. A penis prosthesis as set forth in claim 4 characterized in that a cap is fitted onto an end of the core.

6. A penis prosthesis as set forth in claim 4 characterized in that the portion with the central bore forms the distal end of the prosthesis.

7. A penis prosthesis as set forth in claim 4 characterized in that the portion with the central bore forms the proximal end of the prosthesis.

8. A penis prosthesis as set forth in claim 4 characterized in that there is provided a middle portion having a tubular extension portion at both ends, and a proximal portion and a distal portion each having a respective bore for receiving ends of the core in the middle portion.

9. A penis prosthesis as set forth in claim 3 characterized in that the sleeve has an inner layer which comprises a material harder than said implantable material and which is disposed around the core.

10. A penis prosthesis as set forth in claim 3 characterized in that the sleeve has an inner layer which comprises a material harder than said implantable material and which is disposed around the core, but radially spaced from the outer layer.

11. A penis prosthesis as set forth in claim 10 characterized in that a fluid is disposed in the space between the inner and outer layers.

12. A penis prosthesis as set forth in claim 1 characterized in that the rod member has a soft distal portion, a stiffer middle portion and a very stiff proximal portion.

* * * * *